United States Patent
Li et al.

(10) Patent No.: US 11,976,986 B2
(45) Date of Patent: May 7, 2024

(54) PREDICTIVE ELECTRONIC THERMOMETER CIRCUIT STRUCTURE CAPABLE OF TEMPERATURE COMPENSATION

(71) Applicant: CRM ICBG (WUXI) CO., LTD., Jiangsu (CN)

(72) Inventors: Fang Li, Jiangsu (CN); Tianping Shen, Jiangsu (CN)

(*) Notice: Subject to any disclaimer, the term of this patent is extended or adjusted under 35 U.S.C. 154(b) by 0 days.

(21) Appl. No.: 17/918,091

(22) PCT Filed: Jul. 2, 2021

(86) PCT No.: PCT/CN2021/104295
§ 371 (c)(1),
(2) Date: Oct. 10, 2022

(87) PCT Pub. No.: WO2022/142237
PCT Pub. Date: Jul. 7, 2022

(65) Prior Publication Data
US 2023/0332959 A1     Oct. 19, 2023

(30) Foreign Application Priority Data
Dec. 29, 2020  (CN) .......................... 202011598885.1

(51) Int. Cl.
| | | |
|---|---|---|
| *G01K 7/42* | (2006.01) | |
| *G01K 1/20* | (2006.01) | |
| *G01K 7/02* | (2021.01) | |
| *G01K 7/32* | (2006.01) | |

(52) U.S. Cl.
CPC ................. *G01K 7/42* (2013.01); *G01K 1/20* (2013.01); *G01K 7/021* (2013.01); *G01K 7/32* (2013.01)

(58) Field of Classification Search
CPC ............. G01K 1/20; G01K 7/021; G01K 7/32
USPC ........................................ 374/163, 170, 183
See application file for complete search history.

(56) References Cited

U.S. PATENT DOCUMENTS

| | | | | |
|---|---|---|---|---|
| 4,475,823 A | * | 10/1984 | Stone | G01K 15/00 |
| | | | | 374/1 |
| 4,505,599 A | * | 3/1985 | Nonaka | G01K 7/32 |
| | | | | 377/25 |
| 2008/0117722 A1 | | 5/2008 | Ahuja et al. | |
| 2009/0086788 A1 | | 4/2009 | Khaliullin | |
| 2017/0363662 A1 | * | 12/2017 | Neidorff | G01R 19/0092 |
| 2019/0204253 A1 | * | 7/2019 | Yoo | G01K 7/24 |

FOREIGN PATENT DOCUMENTS

| | | | | | |
|---|---|---|---|---|---|
| CN | 1187243 A | | 7/1998 | | |
| CN | 1289040 A | | 3/2001 | | |
| CN | 1370982 A | | 9/2002 | | |
| CN | 101124464 A | * | 2/2008 | | G01K 7/42 |
| CN | 201488830 U | | 5/2010 | | |
| CN | 103175633 A | | 6/2013 | | |
| CN | 106487332 A | | 3/2017 | | |
| CN | 109067394 A | | 12/2018 | | |
| CN | 111486983 A | | 8/2020 | | |
| JP | H4109132 A | * | 4/1992 | | |
| JP | 2002257639 A | | 9/2002 | | |
| WO | WO-2018167765 A1 | * | 9/2018 | | A61B 5/01 |

\* cited by examiner

*Primary Examiner* — Gail Kaplan Verbitsky
(74) *Attorney, Agent, or Firm* — Global IP Services; Tianhua Gu

(57) ABSTRACT

A predictive electronic thermometer circuit structure capable of temperature compensation is provided, including: a compensation module, a thermometer circuit, and a liquid crystal display (LCD) drive module. The thermometer circuit includes a temperature measurement oscillation circuit and a real measurement module. The compensation module and the real measurement module are connected in parallel between the temperature measurement oscillation circuit and the LCD drive module. The predictive electronic thermometer circuit structure controls the on and off of the compensation module and the real measurement module through a combination logic control switch respectively. When the compensation module is off and the real measurement module is on, an actual measured data is output. When the real measurement module is off and the compensation module is on, a temperature value is output after predictive compensation. The electronic thermometer has a temperature compensation function, and measures the temperature quickly and accurately.

6 Claims, 1 Drawing Sheet

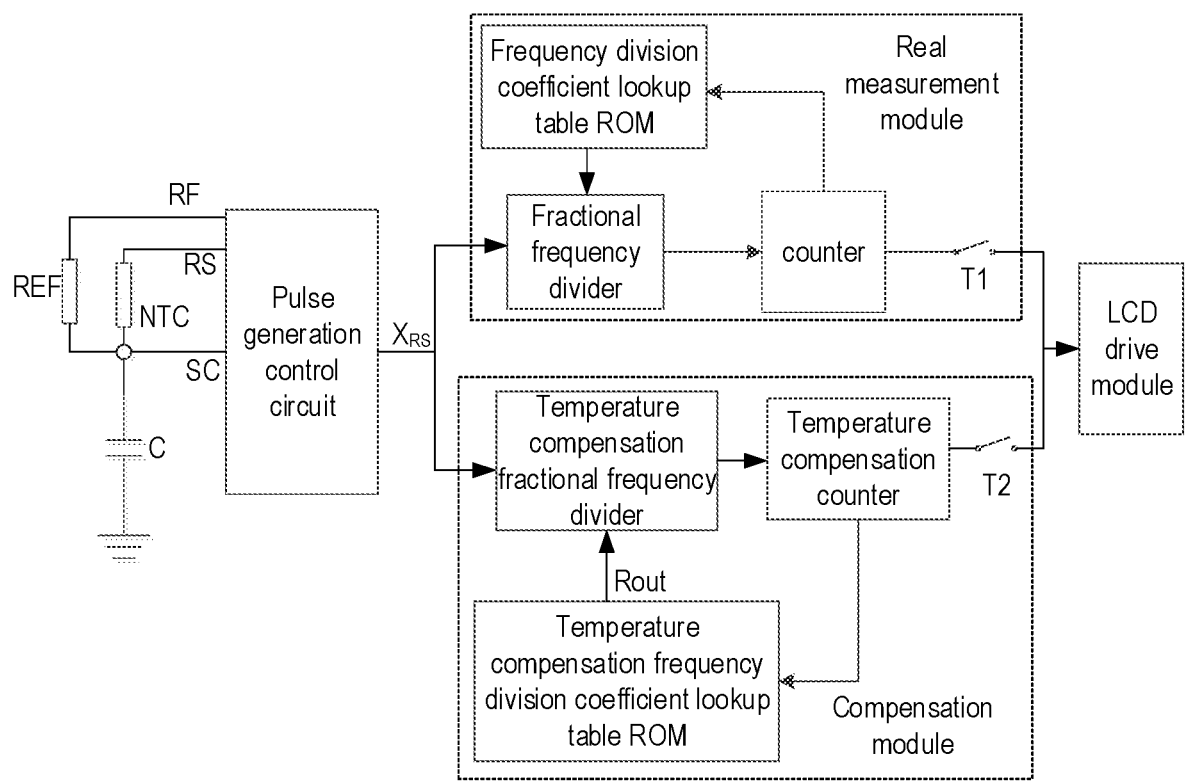

PREDICTIVE ELECTRONIC THERMOMETER CIRCUIT STRUCTURE CAPABLE OF TEMPERATURE COMPENSATION

CROSS REFERENCE TO RELATED PATENT APPLICATION

The present application is the US national stage of PCT/CN2021/104295 filed on 2021 Jul. 02, which claims the priority of the Chinese patent application No. 202011598885.1 filed on 2020 Dec. 29, which application is incorporated herein by reference.

TECHNICAL FIELD

The present disclosure relates to the field of electronic thermometers, and in particular, to a predictive electronic thermometer circuit structure capable of temperature compensation.

BACKGROUND

At present, common thermometers include mercurial thermometers, electronic thermometers, and infrared thermometers.

Mercurial thermometers are traditional thermometers, which are inexpensive and easy to use. The mercurial thermometers are placed on a part to be measured and are left for about 5 minutes, and then a temperature value is read from the mercurial thermometers. The electronic thermometers are placed on a part to be measured and are left for about half a minute, and then a temperature value is read from the electronic thermometers when a beeping alarm is heard. Compared with above thermometers, measurement time of the infrared thermometers is shorter, e.g., the body temperature can be measured in a few seconds by the infrared thermometers. The infrared thermometers include contact infrared thermometers and non-contact infrared thermometers. Because the infrared thermometers are expensive and inconvenient to carry, the current commonly used home thermometers are the mercurial thermometers and the electronic thermometers.

However, there are many shortcomings in the mercurial thermometers, for example, the measurement time is long, the fragile glass material is easy to be broken, and leaked mercury after a mercurial thermometer is broken may cause pollution to the environment, which is not good for health. In 2007, the European Parliament had passed legislation to ban the use of mercury-containing thermometers in EU countries. By the end of 2007, 13 states of U.S. had passed legislation to ban the use of mercury-containing thermometers. There is an inevitable trend that mercurial thermometers will be eliminated, and electronic thermometers become the preferred product to replace mercurial thermometers.

Compared with the infrared thermometers, the measurement time of the electronic thermometers is longer. The measurement time required for different brands of electronic thermometers is also different, ranging from 30 seconds to more than 3 minutes. The disadvantage of shortened measurement time is inaccurate measurement.

For electronic thermometers, when the temperature shown in a screen is not changed in a preset time period, the temperature is considered stable, and the measurement is finished and a beeping alarm is transmitted. The preset time period can be selected by controlling the binding of pins, for example, there are four common modes, e.g., 4 s, 8 s, 16 s, 32 s. In order to achieve the effect of fast temperature measurement, the measurement time is shorten, that is, a short time period is selected as the preset time period by the manufacturers. This shortens the measurement time, but the measurement error will be large.

SUMMARY

The present disclosure provides a predictive electronic thermometer circuit structure capable of temperature compensation.

The predictive electronic thermometer circuit structure capable of temperature compensation includes: a compensation module; a thermometer circuit, where the thermometer circuit includes a temperature measurement oscillation circuit and a real measurement module; and a liquid crystal display (LCD) drive module; where the compensation module and the real measurement module are connected in parallel between the temperature measurement oscillation circuit and the LCD drive module; where the predictive electronic thermometer circuit structure controls on and off of the compensation module and the real measurement module through a combination logic control switch respectively; when the compensation module is off and the real measurement module is on, an actual measured data is output; when the real measurement module is off and the compensation module is on, a temperature value is output after predictive compensation.

In an embodiment, the compensation module includes: a temperature compensation fractional frequency divider, where an input end of the temperature compensation fractional frequency divider is connected to the temperature measurement oscillation circuit; a temperature compensation counter, where an input end of the temperature compensation counter is connected to the temperature compensation fractional frequency divider, an output end of the temperature compensation counter is connected to the LCD drive module through the combinational logic control switch; and a temperature compensation frequency division coefficient lookup table Read-Only Memory (ROM) unit, where an input end of the temperature compensation frequency division coefficient lookup table ROM unit is connected to the temperature compensation counter, and an output end of the temperature compensation frequency division coefficient lookup table ROM unit is connected to the temperature compensation fractional frequency divider.

In an embodiment, the compensation module counts an error ∇T between a measured temperature and an actual temperature T, calculates the number $X_{RS}$ of oscillations, calculates an increased number Nz of oscillations as the temperature increases, calculates a frequency division coefficient lookup table output Rout through the temperature compensation fractional frequency divider, the frequency division coefficient lookup table ROM unit outputs a corresponding frequency division coefficient to the temperature compensation fractional frequency divider according to a current temperature value, the temperature compensation fractional frequency divider outputs 100 pulse signals to the temperature compensation counter after frequency division, and the temperature value is displayed through an LCD drive circuit.

In an embodiment, the temperature measurement oscillation circuit includes a pulse generation control circuit, a reference voltage REF, a temperature sensor NTC and a capacitor, the reference voltage REF and the temperature sensor NTC are connected to the pulse generation control circuit, an end of the reference voltage REF is connected to an end of the temperature sensor NTC and is grounded through the capacitor, the reference voltage REF is connected to the pulse generation control circuit through a reference resistor (RF), the temperature sensor NTC is connected to the pulse generation control circuit through a sensing resistor (RS), and the capacitor is connected to the pulse generation control circuit through an oscillator SC.

In an embodiment, the compensation module calculates the number $X_{RS}$ of oscillations, where the number $X_{RS}$ of oscillations is calculated according to the following formula:

$$X_{RS}^{T+\nabla T} = \frac{R_{RF}}{R_{RS}^{T}} \times X_{RF};$$

where $R_{RF}$ is a reference resistance value, $X_{RS}^{T}$ is a resistance value of the temperature sensor NTC corresponding to the actual temperature T, $X_{RF}$ is the number of oscillations of the oscillator SC when RF is off, and $X_{RS}$ is the number of oscillations of the oscillator SC when RS is off.

In an embodiment, the compensation module calculates the increased number Nz of oscillations as the temperature increases, where the increased number Nz of oscillations as the temperature increases is calculated according to the following formula:

$$N_Z = X_{RS}^{T+\nabla T} - X_{RS}^{T+\nabla T-1}$$

where $\nabla T$ is a compensation value, T is the actual temperature.

In an embodiment, the compensation module calculates the frequency division coefficient lookup table output Rout, where the frequency division coefficient lookup table output Rout is calculated according to the following formula:

$$100 = \frac{255 - R\,out}{512} \times N_Z;$$

where $N_Z$ is the increased number of oscillations as the temperature increases.

The predictive electronic thermometer circuit structure capable of temperature compensation of the present disclosure has many advantages, e.g., simple implementation, fast temperature measurement, and compensation for measurement errors based on a measured temperature. The present disclosure has two sets of counting system, a real measurement mode and a prediction mode can be selected to facilitate production calibration. The electronic thermometer described in the present disclosure has a temperature compensation function, which can measure the temperature quickly and accurately.

BRIEF DESCRIPTION OF THE DRAWINGS

FIG. 1 is a schematic diagram of a predictive electronic thermometer circuit structure capable of temperature compensation according to an embodiment of the present disclosure.

DETAILED DESCRIPTION OF THE PREFERRED EMBODIMENTS

In order to clearly describe the technical content of the present disclosure, the following combined with specific embodiments to be further described.

An electronic thermometer circuit with prediction function is provided. The electronic thermometer circuit has the following features: simple implementation, fast temperature measurement, and compensation for measurement errors based on a measured temperature. Both the temperature compensation function and the real measurement function are realized by two counters and two Read-Only Memories (ROM). A schematic diagram of the circuit is shown in FIG. 1.

On the basis of the existing electronic thermometers, a frequency divider, a counter, a lookup table ROM unit are added to realize the temperature compensation function. When a real measurement mode is selected, a switch T2 is turned off and a switch T1 is turned on through a combination logic control switch, and a liquid crystal display (LCD) screen outputs the data of a real measurement module, which is used to calibrate temperatures in the production of thermometers. When a prediction mode is selected, the switch T1 is turned off and the switch T2 is turned on through the combination logic control switch, and the LCD screen outputs the data of a prediction module, the temperature displayed on the LCD screen is a temperature value after prediction compensation.

The predictive electronic thermometer circuit structure capable of temperature compensation includes a compensation module, a thermometer circuit, and an LCD drive module. The thermometer circuit includes a temperature measurement oscillation circuit and a real measurement module. The compensation module and the real measurement module are connected in parallel between the temperature measurement oscillation circuit and the LCD drive module. The predictive electronic thermometer circuit structure controls the on and off of the compensation module and the real measurement module through the combination logic control switch respectively. When the compensation module is off and the real measurement module is on, an actual measured data is output. When the real measurement module is off and the compensation module is on, a temperature value is output after predictive compensation.

The compensation module includes a temperature compensation fractional frequency divider, a temperature compensation counter, and a temperature compensation frequency division coefficient lookup table ROM unit. An input end of the temperature compensation fractional frequency divider is connected to the temperature measurement oscillation circuit. An input end of the temperature compensation counter is connected to the temperature compensation fractional frequency divider, an output end of the temperature compensation counter is connected to the LCD drive module through the combinational logic control switch. An input end of the temperature compensation frequency division coefficient lookup table ROM unit is connected to the temperature compensation counter, and an output end of the temperature compensation frequency division coefficient lookup table ROM unit is connected to the temperature compensation fractional frequency divider.

The temperature measurement oscillation circuit includes a pulse generation control circuit, a reference voltage REF, a temperature sensor NTC, and a capacitor. The reference voltage REF and the temperature sensor NTC are connected in parallel with the pulse generation control circuit, an end of the reference voltage REF is connected to an end of the temperature sensor NTC and is grounded through the capacitor, the reference voltage REF is connected to the pulse generation control circuit through a reference resistor (RF), the temperature sensor NTC is connected to the pulse generation control circuit through a sensing resistor (RS), and the capacitor is connected to the pulse generation control circuit through an oscillator SC.

The principle of the compensation module is as follows:

Firstly, according to the clinical data, an error ∇T between the measured value and the actual temperature T is counted when the electronic thermometer is used to measure the temperature. Where the measured value is equal to the sum of the actual temperature T and the error ∇T, and ∇T is a compensation value. In the electronic thermometer, each time RS is turned on, different numbers $X_{RS}$ of oscillations of the oscillator SC correspond to different temperature values through a frequency division coefficient lookup table ROM. To realize the temperature compensation function, the compensation value ∇T is added to the temperature value T corresponding to the number $X_{RS}$ of oscillations, thus when the actual temperature is T, a display value on the LCD screen is T+∇T. This can be achieved by modifying the output Rout of the frequency division coefficient lookup table ROM unit.

When the number $X_{RS}$ of oscillations of the oscillator SC is calculated, the temperature T corresponding to the $X_{RS}$ is changed to the predicted value T+∇T:

$$X_{RS}^{T+\nabla T} = \frac{R_{RF}}{R_{RS}^T} \times X_{RF}$$

$X_{RF}$ is the number of oscillations of the oscillator SC when the RF is off, $X_{RS}$ is the number of oscillations of the oscillator SC when the RS is off, $R_{RF}$ is a reference resistance value, $R_{RS}^T$ is a resistance value of the temperature sensor NTC corresponding to the actual temperature T.

When the screen display value varies from 32° C. to 43° C. (the compensated temperature), the increased number Nz of oscillations is calculated for every 1° C. increase in temperature. The formula is as follows:

$$N_Z = X_{RS}^{T+\nabla T} - X_{RS}^{T+\nabla T-1}$$

The output Rout of the temperature compensation frequency division coefficient lookup table ROM unit is calculated, according to the following formula corresponding to the temperature compensation fractional divider:

$$100 = \frac{255 - R_{out}}{512} \times N_Z$$

The frequency division coefficient lookup table ROM unit outputs a corresponding frequency division coefficient to the fractional frequency divider according to the current temperature value counted by the counter. The fractional frequency divider outputs 100 pulse signals to the counter after frequency division. The counter adds 1 to each pulse, and the corresponding displayed temperature is 0.01° C., which is then displayed by the LCD drive circuit.

In an example, $X_{RF}$=6455, $R_{RF}$=30KΩ, the resistance value of the temperature sensor NTC is 503ET, a starting temperature of the electronic thermometer is 32° C. (when the temperature is below 32° C., the electronic thermometer displays Lo and does not display the temperature value), the temperature compensation value is taken as shown in the following table, then the calculated value $N_Z$ is as follows after the temperature compensation value is added:

| Compensated temperature (° C.) | Temperature compensation value (° C.) | Actual temperature (° C.) | Number $N_z$ of oscillations | Rout |
|---|---|---|---|---|
| 32 | 2.5 | 29.5 | 4715 | |
| 33 | 2.5 | 30.5 | 205.1077 | 5 |
| 34 | 2.5 | 31.5 | 213.3112 | 15 |
| 35 | 2 | 33 | 334.9824 | 102 |
| 36 | 1 | 35 | 477.2651 | 148 |
| 37 | 0 | 37 | 510.1934 | 154 |
| 38 | 0 | 38 | 269.7016 | 65 |
| 39 | 0 | 39 | 279.3967 | 71 |
| 40 | 0 | 40 | 289.3989 | 78 |
| 41 | 0 | 41 | 296.3741 | 85 |
| 42 | 0 | 42 | 313.7377 | 89 |
| 43 | 0 | 43 | 320.915 | 96 |

The predictive electronic thermometer circuit structure capable of temperature compensation of the present disclosure has many advantages, e.g., simple implementation, fast temperature measurement, and compensation for measurement errors based on a measured temperature. The present disclosure has two sets of counting system, a real measurement mode and a predictive mode can be selected to facilitate production calibration. The electronic thermometer described in the present disclosure has a temperature compensation function, which can measure the temperature quickly and accurately.

In this specification, the present disclosure has been described with reference to particular embodiments thereof. However, it is clear that various modifications and transformations can still be made without departing from the spirit and scope of the present disclosure. Accordingly, the specification and accompanying drawings should be considered as illustrative rather than limiting.

What is claimed is:

1. An electronic thermometer circuit system having compensation module for accurate measuring, comprising:
    a compensation module;
    a thermometer circuit comprising a temperature measurement oscillation circuit and a real measurement module; and
    a liquid crystal display (LCD) drive module;
    wherein the compensation module and the real measurement module are connected in parallel between the temperature measurement oscillation circuit and the LCD drive module;
    wherein the electronic thermometer circuit structure controls on and off of the compensation module and the real measurement module through a combination logic control switch respectively; when the compensation module is off and the real measurement module is on, an actual measured data is output; when the real measurement module is off and the compensation module is on, a temperature value is output after compensation;
    wherein the compensation module comprises:
        a temperature compensation fractional frequency divider, an input end of the temperature compensation fractional frequency divider is connected to the temperature measurement oscillation circuit;
        a temperature compensation counter, an input end of the temperature compensation counter is connected to the temperature compensation fractional frequency divider, an output end of the temperature compensation counter is connected to the LCD drive module through the combinational logic control switch; and a temperature compensation frequency division coefficient lookup table Read-Only Memory (ROM) unit, an input end of the temperature compensation frequency division coefficient lookup table ROM unit is connected to the temperature compensation counter, and an output end of the temperature compensation frequency division coefficient lookup table ROM unit is connected to the temperature compensation fractional frequency divider.

2. The electronic thermometer circuit system having compensation module for accurate measuring according to claim 1, wherein the compensation module counts an error $\nabla T$ between a measured temperature and an actual temperature T, calculates the number $X_{RS}$ of oscillations, calculates an increased number Nz of oscillations as the temperature increases, calculates a frequency division coefficient lookup table output Rout through the temperature compensation fractional frequency divider, the frequency division coefficient lookup table ROM unit outputs a corresponding frequency division coefficient to the temperature compensation fractional frequency divider according to a current temperature value, the temperature compensation fractional frequency divider outputs 100 pulse signals to the temperature compensation counter after frequency division, and the temperature value is displayed through an LCD drive circuit.

3. The electronic thermometer circuit system having compensation module for accurate measuring according to claim 1, wherein the temperature measurement oscillation circuit comprises a pulse generation control circuit, a reference voltage REF, a temperature sensor NTC and a capacitor, wherein the reference voltage REF and the temperature sensor NTC are connected in parallel with the pulse generation control circuit, an end of the reference voltage REF is connected to an end of the temperature sensor NTC, and is grounded through the capacitor, the reference voltage REF is connected to the pulse generation control circuit through a reference resistor (RF), the temperature sensor NTC is connected to the pulse generation control circuit through a sensing resistor (RS), and the capacitor is connected to the pulse generation control circuit through an oscillator SC.

4. The electronic thermometer circuit system having compensation module for accurate measuring according to claim 2, wherein the compensation module calculates the number $X_{RS}$ of oscillations, wherein the number $X_{RS}$ of oscillations is calculated according to the following formula:

$$X_{RS}^{T+\nabla T} = \frac{R_{RF}}{R_{RS}^{T}} \times X_{RF};$$

wherein $R_{RF}$ is a reference resistance value, $R_{RS}^{T}$ is a resistance value of the temperature sensor NTC corresponding to the actual temperature T, $X_{RF}$ is the number of oscillations of the oscillator SC when RF is off, and $X_{RS}$ is the number of oscillations of the oscillator SC when RS is off.

5. The electronic thermometer circuit system having compensation module for accurate measuring according to claim 2, wherein the compensation module calculates the increased number Nz of oscillations as the temperature increases, wherein the increased number Nz of oscillations as the temperature increases is calculated according to the following formula:

$$N_Z = X_{RS}^{T+\nabla T} - X_{RS}^{T+\nabla T-1}$$

wherein $\nabla T$ is a compensation value, T is the actual temperature.

6. The electronic thermometer circuit system having compensation module for accurate measuring according to claim 2, wherein the compensation module calculates the frequency division coefficient lookup table output Rout, wherein the frequency division coefficient lookup table output Rout is calculated according to the following formula:

$$100 = \frac{255 - R\text{out}}{512} \times N_Z;$$

wherein $N_Z$ is the increased number of oscillations as the temperature increases.

* * * * *